United States Patent [19]

Pelosi, Jr.

[11] 4,128,550

[45] Dec. 5, 1978

[54] 1-METHYL-4-PIPERIDYL 5-PHENYL-2-FUROATES

[75] Inventor: Stanford S. Pelosi, Jr., Norwich, N.Y.

[73] Assignee: Morton-Norwich Products, Inc., Norwich, N.Y.

[21] Appl. No.: 879,077

[22] Filed: Feb. 21, 1978

[51] Int. Cl.$^2$ ............................................. C07D 405/12
[52] U.S. Cl. ..................................... 546/214; 424/267
[58] Field of Search ................................. 260/293.67

[56] References Cited

U.S. PATENT DOCUMENTS 3,856,825  12/1974  Wright et al. ..................... 260/345.7

FOREIGN PATENT DOCUMENTS 74-18864  2/1974  Japan ................................... 260/293.67

OTHER PUBLICATIONS

Goldenberg, " Arch. Int. Pharmacodyn. Ther.," (1976), vol. 222(1), pp. 27–39.

Primary Examiner—John D. Randolph
Assistant Examiner—Robert T. Bond
Attorney, Agent, or Firm—Anthony J. Franze

[57] ABSTRACT

The title compounds are useful as anti-inflammatory agents.

3 Claims, No Drawings

1-METHYL-4-PIPERIDYL 5-PHENYL-2-FUROATES

This invention is concerned with chemical compounds. More particularly, it is concerned with compounds of the formula:

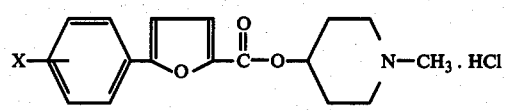

wherein X is nitro or chloro. These compounds are useful as anti-inflammatory agents. When administered perorally to rats at a dose of about 300 mg/kg, edema elicited by the administration of carrageenin is inhibited.

The compounds of this invention may be compounded in a variety of pharmaceutical dosage forms such as tablets, elixirs, solutions, capsules, and the like using excipients and adjuvants commonly available.

In order that this invention may be readily available to and understood by those skilled in the art, the following examples are supplied:

EXAMPLE I

1-Methyl-4-piperidyl 5-(p-chlorophenyl)-2-furoate Hydrochloride

To a stirring solution of 40 g (0.35 mole) of N-methyl-4-piperidol in 400 ml of toluene was added portionwise 84 g (0.35 mole) of 5-(p-chlorophenyl)-2-furoyl chloride with the temperature rising to 50°. The resulting mixture was heated at 90° for 1 hour and then stirred at room temperature overnight. The solid was filtered, suspended in H$_2$O and acidity assured by the addition of a few drops of hydrochloric acid. The insoluble material was filtered. The filtrate was made basic by the addition of concentrated NH$_4$OH. The resulting solid was filtered and added to 1500 ml of ether with dissolution. The solution was treated with Darco, dried with MgSO$_4$ and filtered. The filtrate was treated with ethereal HCl. A "sticky" solid formed from which the ether was decanted. The semi-solid was triturated in ethanol with a white solid forming which weighed 50 g (40%) after drying. An analytical sample was prepared by drying a sample at room temperature in the vacuum pistol, m.p. 239°–240°.

Anal. Calcd. for C$_{17}$H$_{18}$ClNO$_3$·HCl: C, 57.31; H, 5.38; N, 3.93. Found: C, 57.44; H, 5.44; N, 3.74.

The 5-(p-chlorophenyl)-2-furoyl chloride used in this example was obtained by reaction of 5-(p-chlorophenyl)-2-furoic acid and thionyl chloride.

EXAMPLE II

1-Methyl-4-piperidyl 5-(p-Nitrophenyl)-2-furoate Hydrochloride

A mixture of 57 g (0.25 mole) of 5-(p-nitrophenyl)-2-furoic acid and 120 ml of SOCl$_2$ was refluxed for 3½ hours with dissolution. The SOCl$_2$ was removed on the Calab evaporator. Benzene was added to the solid residue and was then removed on the Calab evaporator. The resulting solid was added portionwise to a stirring solution of 29 g (0.25 mole) of N-methyl-4-piperidinol in 250 ml of toluene becoming exothermic (60° C). The reaction mixture was heated on a steam bath for 1 hour and then allowed to stand overnight. The crude solid was filtered and then stirred in water. Some insoluble material was filtered and discarded. The filtrate was made basic with concentrated NH$_4$OH and the resulting solid was extracted with 5,000 ml of ethyl acetate. The ethyl acetate was dried over MgSO$_4$ and treated with HCl gas. The resulting solid was filtered, suspended in refluxing ethanol, cooled and filtered to yield 22 g (24%). An analytical sample was obtained by drying a sample of the above product in a vacuum pistol at the temperature of refluxing water for ca. 60 hours, m.p. 266°–268° C (Mel-Temp).

Anal. Calcd. for C$_{17}$H$_{18}$N$_2$O$_5$·HCl: C, 55.66; H, 5.22; N, 7.64. Found: C, 55.52; H, 5.26; N, 7.63.

What is claimed is:

1. A compound of the formula:

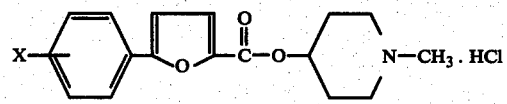

wherein X is nitro or chloro.

2. The compound 1-methyl-4-piperidyl 5-(p-chlorophenyl)-2-furoate hydrochloride.

3. The compound 1-methyl-4-piperidyl 5-(p-nitrophenyl)-2-furoate hydrochloride.

* * * * *